(12) United States Patent
Lee

(10) Patent No.: US 6,921,365 B2
(45) Date of Patent: Jul. 26, 2005

(54) REMOTE NON-INVASIVE BIOFEEDBACK DIAGNOSTIC SYSTEM BASED ON PATIENT IMAGE

(75) Inventor: Hanmyung Lee, Seoul (KR)

(73) Assignee: Clinictech, Inc., Austin, TX (US)

( * ) Notice: Subject to any disclaimer, the term of this patent is extended or adjusted under 35 U.S.C. 154(b) by 112 days.

(21) Appl. No.: 10/413,279

(22) Filed: Apr. 14, 2003

(65) Prior Publication Data

US 2004/0204632 A1 Oct. 14, 2004

(51) Int. Cl.$^7$ .................................................. A61B 5/00
(52) U.S. Cl. ...................................... 600/300; 128/905
(58) Field of Search ............................... 600/300–301, 600/544–545, 559, 558; 128/905, 920, 898; 434/236–238

(56) References Cited

U.S. PATENT DOCUMENTS

| | | | |
|---|---|---|---|
| 4,031,883 A | | 6/1977 | Fehmi |
| 4,195,626 A | | 4/1980 | Schweizer |
| 5,415,167 A | | 5/1995 | Wilk |
| 5,746,205 A | * | 5/1998 | Virsu et al. ............... 600/545 |
| 5,755,230 A | * | 5/1998 | Schmidt et al. ........... 600/544 |
| 6,173,068 B1 | | 1/2001 | Prokoski |
| 6,208,374 B1 | | 3/2001 | Clinch |
| 6,224,549 B1 | * | 5/2001 | Drongelen ................. 600/559 |
| 6,236,884 B1 | * | 5/2001 | Hunter et al. ............. 600/544 |
| 6,306,077 B1 | * | 10/2001 | Prabhu et al. ............. 128/898 |
| 6,501,849 B1 | | 12/2002 | Gupta |
| 6,549,805 B1 | * | 4/2003 | Nesterov et al. .......... 600/545 |

FOREIGN PATENT DOCUMENTS

EP 1 062 907 A1 12/2000

* cited by examiner

*Primary Examiner*—Max F. Hindenburg
*Assistant Examiner*—Michael C Astorino
(74) *Attorney, Agent, or Firm*—Boris Leschinsky

(57) ABSTRACT

A non-invasive remote diagnostic system includes a central processing unit (CPU) adapted to feed an image of a patient such as a digital photograph to be displayed to an operator by a first computer monitor. A second computer monitor is displaying a realistic outline of a target area of diagnostic interest such as an outline of a human organ or a particular portion thereof. These two monitors together with a CPU are adapted to induce a state of heightened consciousness and intuition of a system operator. A detecting/evaluating unit is sensing non-invasively the operator's biofeedback response while the operator is exposed to the images. The biofeedback response is converted to an electrical signal and is fed back into the CPU to compare against a predetermined database of similar signals obtained from volunteers with known diseases. The biofeedback signal allows a non-invasive remote diagnosis of a patient's state of health.

12 Claims, 3 Drawing Sheets

REMOTE NON-INVASIVE BIOFEEDBACK DIAGNOSTIC SYSTEM BASED ON PATIENT IMAGE

FIELD AND BACKGROUND OF THE INVENTION

The present invention relates generally to a remote biofeedback medical diagnostic system. More particularly, the system of the invention utilizes a noninvasive biofeedback signal obtained by the system from the operator exposed to the images of the patient and the target area to determine pathological conditions of the patient. The term "operator" is used interchangeably with the term "user" throughout this description to describe a human person using the biofeedback system. The biofeedback signal is generated subconsciously by the operator and is based on device enhanced intuition.

A variety of medical diagnostic systems based on biofeedback are known in the art to determine the pathophysiological status of the patient in general and to diagnose a variety of ailments or the condition of specific organs.

One example of a comprehensive biofeedback device is described by Schweizer in the U.S. Pat. No. 4,195,626 and includes application of a variety of audible, visual, electrical or tactile stimuli in a specially designed biofeedback chamber. Moreover, a microprocessor controlled rhythmical pattern of these stimuli is proposed and is adjusted based on the patient's own reactions.

An even more sophisticated system involves detecting the patient's electrical brainwaves via electroencephalogram or EEG as measured from a number of electrodes attached to the patient's scalp. Several examples of EEG based biofeedback devices are worth mentioning here among a large number of such systems described in the prior art.

A multiple channel biofeedback computer is described in the U.S. Pat. No. 4,031,883 by Fehmi et al. which contains a number of monopolar electrical contacts applied to the scalp and the body of the patient and a computer for collecting, filtering and amplifying the electrical signals therefrom. The overall feedback signal is then presented back to the patient to create awareness of the function being monitored of for other purposes.

All of the above diagnostic systems involve collecting and analyzing a biofeedback signal obtained from a patient. This diagnostic method is not available if the patient is located far from the diagnostic laboratory. The need exists for a noninvasive diagnostic system allowing remote diagnosis of the patient's condition.

Patient's image may be transmitted using a variety of known means from the location of the patient to the location of the diagnostic system. Generally, image-based diagnostic systems are also known. Gupta, for example, describes a system for image-based diagnosis in the U.S. Pat. No. 6,501,849. This system is used for computer-based identification of technical problems in the field and has not been used for any medical application. A central computer stores a number of normal images of various machines and compares them to the images fed from a remote location.

Telepathology system is depicted in the U.S. Pat. No. 6,208,374 by Clinch to include a high resolution scanning of a pathology specimen transmitted to a remote location for diagnosis by a specialist. A somewhat similar system for scanning selected internal organs is described by Wilk in the U.S. Pat. No. 5,415,167.

A system for remotely transmitting a view of a patient to a clinician is described in the European Patent application No. EP 1062907 by Symes. The image may be a still or video image. Clinician can in turn detect such abnormalities as a cervical cancer.

Finally, a system for acquiring and transmitting to a remote location of a facial thermograph of a person is described in the U.S. Pat. No. 6,173,068. The thermograph is used for identification purposes, diagnosis and treatment evaluation.

These remote diagnosis systems of the prior art are based on a simple transmission of the visual information from the patient to a specialist who is then looking at the visual data to determine the diagnosis of a particular organ of a patient.

The need exists for a remote diagnosis system allowing a comprehensive diagnosis of the entire human body as well as individual diagnosis of a particular organ or a number of organs of the patient.

SUMMARY OF THE INVENTION

Accordingly, it is an object of the present invention to overcome these and other drawbacks of the prior art by providing a novel remote non-invasive diagnostic system based on the biofeedback collected from the operator of the system. This biofeedback is collected by the system while the operator is being influenced by a predetermined series of stimuli and focuses on both the image of the patient as well as an outline of a specific target area of the diagnosis such as an outline of a particular organ.

It is another object of the present invention to provide a remote diagnostic system capable of inducing the heightened state of consciousness in the operator so that his intuition is enhanced for a more accurate diagnosis.

It is a further object of the present invention to provide a remote diagnostic system capable of objective determination of the medical status of patient in general as well as his specific organs and even parts of organs and tissues.

It is yet further object of the present invention to build the reference database by which the signals acquired via consciousness induction of the operator are evaluated and analyzed.

The system of the invention is based on the discovery that if the consciousness and intuition of the operator is correctly induced to focus on a specific target (for example, specific organ of certain patient), certain biofeedback signal changes occur around the operator. An electric device specially designed for this purpose can then detect these changes. And it was also observed that these changes were closely related with the state of a specific target organ of patient at the time when the test was performed.

The remote diagnostic system of the invention includes a CIU (Consciousness Induction Unit), a DEU (Detection/Evaluation Unit) and a CPU (Central Processing Unit). In the most preferred configuration, the consciousness induction unit is composed of various video displaying devices which can provide the appropriate visual stimulation to the operator for inducing his consciousness and intuition in order to diagnose the state of a specific organ/tissue of the patient remotely. The detection/evaluation unit converts the diagnostic results, which are acquired from the operator in the state of induced consciousness and heightened intuition to an electric signal. The operation of these two units is controlled and coordinated by the central processing unit, which also accumulates a database of signals from the detection/evaluation unit and stores the acquired digital data for future analysis.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE PREFERRED EMBODIMENT OF THE INVENTION

A detailed description of the present invention follows with reference to accompanying drawings in which like elements are indicated by like reference letters and numerals.

Figure 1:
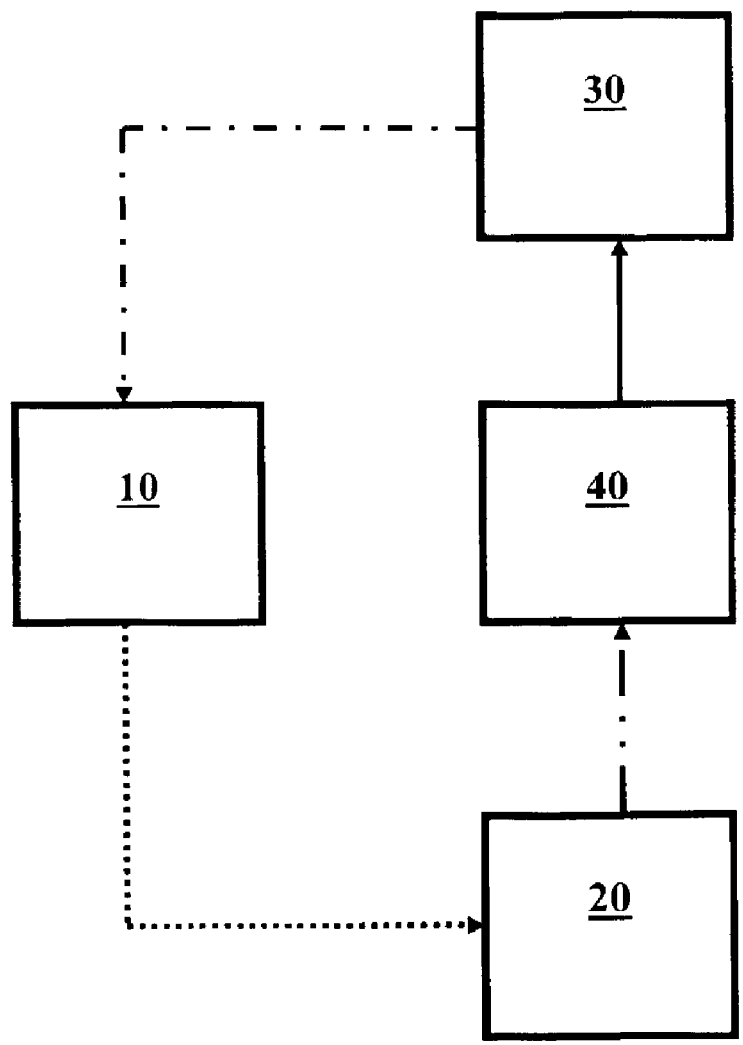
FIG. 1 is a general block-diagram of the remote diagnostic system of the present invention.

FIG. 1 shows the main block-diagram of the proposed system of the present invention, its components and their relationship to each other. A CPU unit 10 is a server computer and contains a situation-generating sub-system in a computer readable memory similar to that described in the U.S. Pat. No. 6,549,805 assigned to the same assignee as the present invention and incorporated herein by reference in its entirety. It is designed to output a predetermined patient-specific series of visual images and transmit them through CIU unit 20 to operator 40. CPU unit 10 is also connected to DEU unit 30 to receive electric biofeedback signals therefrom. These signals are stored in database system of CPU unit 10.

The main principle of the diagnostic system of the invention is to expose the operator to two sets of visual stimulation images: one is the image of the patient and the other is the visual outline of the target area of diagnostic interest. The operator is placed in a state of heightened consciousness and intuition while observing these images. A proprietary biofeedback system described below is used to collect the biofeedback signals from the operator as a reaction to the visual stimulation caused by the image of the patient and the outline of the target area. That biofeedback signal is then transformed into an electrical signal and fed back into the CPU unit 10.

Of course, it is to be understood that the system of the invention can be used in such a way that it is the patient himself rather than his image, who is exposed to the observation of the operator, still along with the outline of the target area of interest. In that case, the system is still advantageous due to the non-invasive nature of the diagnosis but the remote feature is lost.

Figure 2:
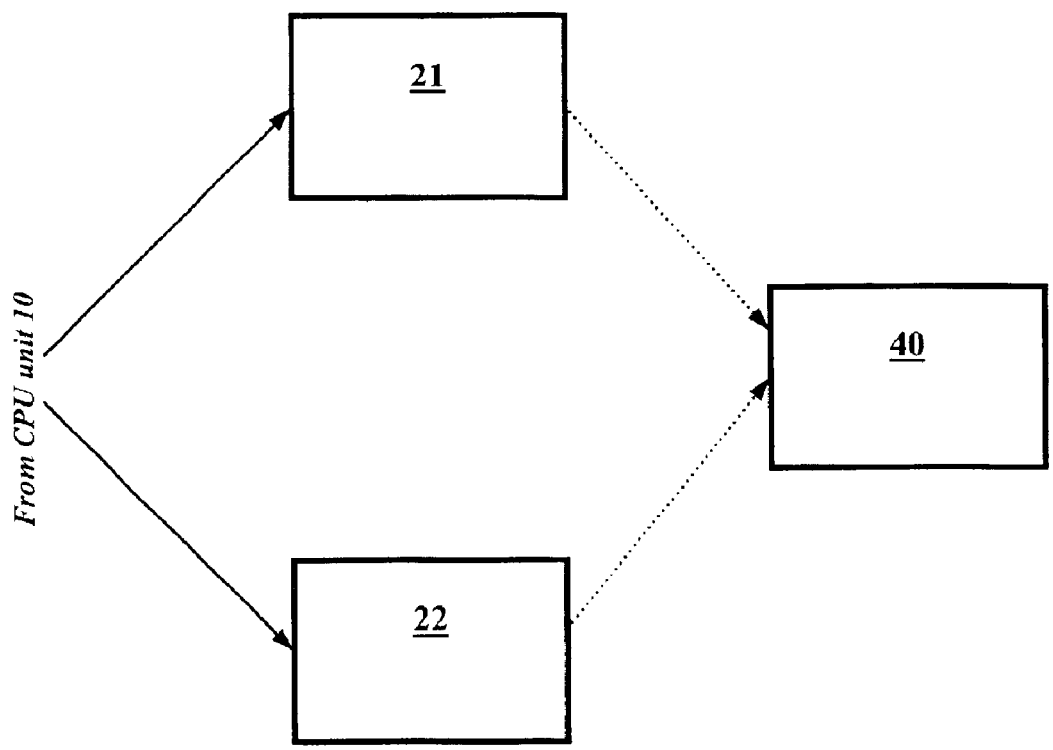
FIG. 2 is a general block diagram of consciousness and intuition induction unit of the system.

FIG. 2 shows the general block diagram of CIU (Consciousness Induction) unit 20. CIU unit 20 is composed of a first and a second means for visual display 21 and 22 such as for example computer monitors. In a variation of the system of the present invention (not shown on the drawings), a single computer monitor can be used to display both images side-by-side. Note that other commonly known means can also be used for this purpose such as a stand designed to expose a paper image of the patient (photograph, drawing, painting, sketch and alike). A slide projector is yet another example of the visual display means. The advantage of the computer monitor is that a number of digital images can be shown to the operator in a rapid progression so several diagnostic sessions can be conducted in a short period of time.

A first computer monitor 21 is designed to display a digital photograph of patient, while a second computer monitor 22 is designed to display an outline of the target area of diagnostic interest. Such outline can be a general picture or sketch of an organ/tissue for which the diagnosis should be performed. The outline has to have enough resolution that the operator recognizes the area of interest. Note that it is enough to display simply a general outline of the organ and not a specific organ of a particular patient.

The graphic data, which should be displayed on these two monitors 21 and 22 and can be transmitted from CPU unit 10 via a video cable. During the diagnosis process of a certain patient, the first monitor 21 displays the image of a digital photograph of the patient at all time, while the second monitor 22 keeps changing its displaying contents from one organ/tissue to the other organ/tissue of interest. It is also possible to conduct a diagnosis of various sections of a particular organ as they can be highlighted in a succession of images. For example, if the function of liver and lung of a certain patient should be diagnosed, the monitor 21 displays the image of a digital photograph of the patient and the second monitor 22 initially displays the image of a realistic picture of a liver. At the beginning, a certain portion (such as a right lobe) of the liver is highlighted. Next, another portion (such as a left lobe) of liver is highlighted, and so on. With this method, every part of the liver is highlighted in turn. When all portions of the liver have been highlighted, the second monitor 22 changes its content to the image of a realistic picture of a lung. Again, one portion (such as a right upper lobe for example) of the lung is highlighted and then another portion (such as a right lower lobe) is highlighted, and so on. During the diagnosis process, the operator should stare at and concentrate on both the digital photograph of the patient and the highlighted portion in the picture of the target organ/tissue which is periodically changing as time goes on. In this way, operator's consciousness and intuition is focused and induced to diagnose the functional state of the corresponding organ/tissue of interest of a particular patient.

In addition, supplemental means of enhancing intuition and inducing consciousness can be used in parallel with the visual means (not shown on the drawings). Such supplemental means are designed to produce a series of stimuli to enhance the sensitivity of the biofeedback signals from the operator depending on the purpose of evaluation. Examples of such supplemental means include those to produce stimuli such as audio, video, optical, light, electromagnetic and others. These stimuli can be applied to the operator through such peripheral means as monitors, headphones, laser lamps, and radio transmitters.

The function of the DEU unit 30 is to sense the biofeedback responses produced by consciousness induction of the operator 40, and to transform them into digital signals so they can be sent back to the CPU unit 10. One useful example of the DEU is a triggering sensor equipped with a noise generator as described below. The biofeedback response signal in that case is the changes in the noise as effected by the operator. It should be noted here that other biofeedback response sensors of commonly known designs could also be used for the purposes of the invention.

Figure 3:
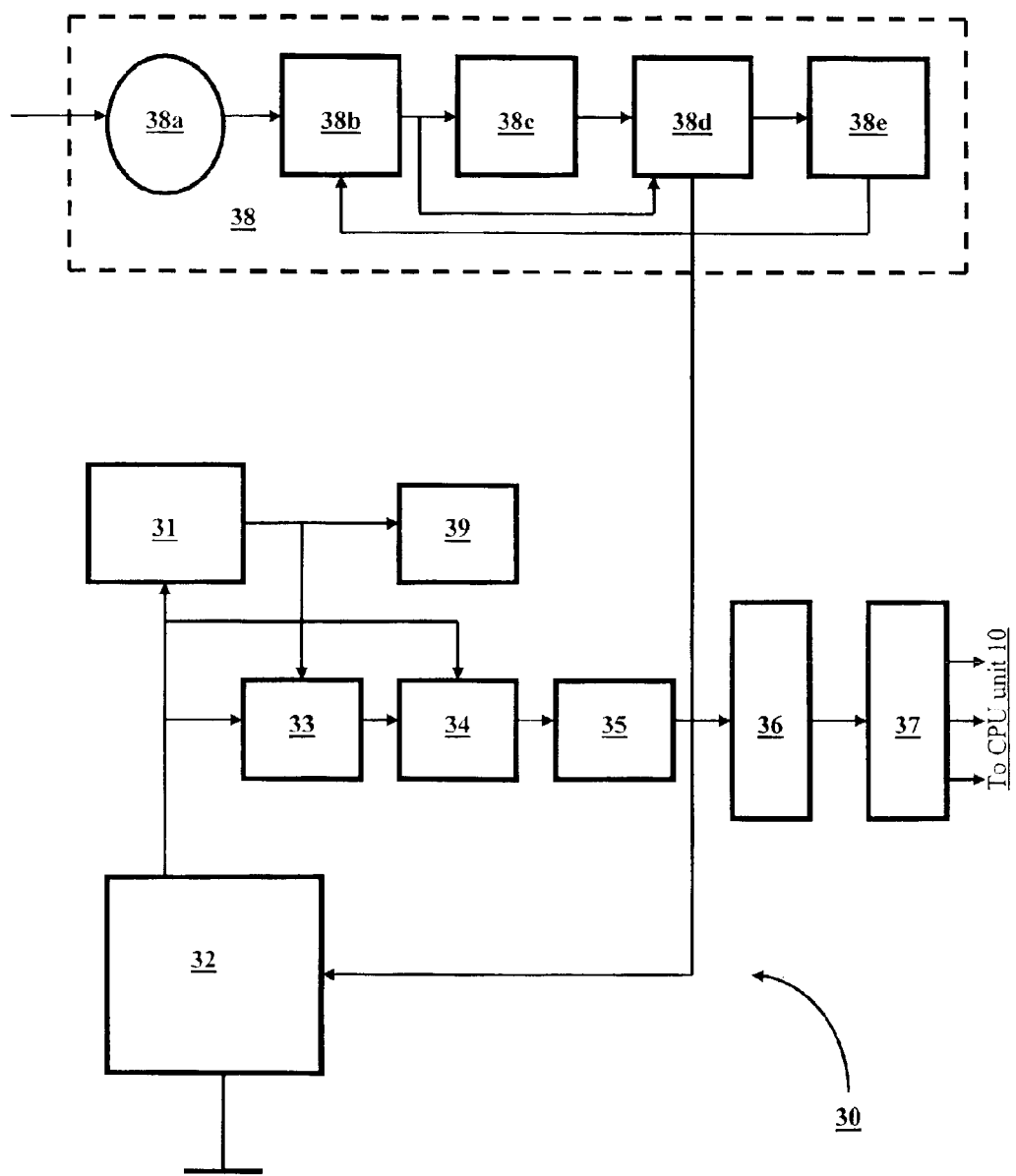
FIG. 3 is a general block diagram of the detection/evaluation unit of the system.

FIG. 3 shows the general block diagram of DEU (Detection and Evaluation) unit 30. DEU unit 30 is also called a triggering sensor and it has been described in detail in the U.S. Pat. No 6,549,805 assigned to the same assignee as the present invention as referenced above. It consists of a sensing element 31, an integrator 32, a source of electrical current 33, a differential amplifier 34, an amplifier 35, a comparator 36, a galvanic decoupling unit 37, and a detector channel 38. The detector channel 38 in turn consists of a logoperiodic antenna 38a, mixer 38b, rectifier 38c, discriminator 38d, and heterodyne 38e.

The triggering sensor includes the sensing element 31 with a commonly known noise generator based for example on the radioelement 2G401V. The sensing element 31 is capable of remotely sensing the biofeedback response of the operator 40 when it is placed in the vicinity thereof. A direct electrical current of an optimized value in the range of only several microamps, preferably between 1 and 5, is provided to power this sensing element 31 by the power supply 39. This current is adjustable and is determined individually during the fine-tuning of the device in-vitro.

Electrical current source 33 consists of an operation amplifier such as for example the type UD25A (made by Voshod company in Kaluga, Russia) and an adjusting element such as a bipolar transistor with low noise coefficient, for example the model KT3107L (made by Eleks company in Alexandrov, Russia) capable of supplying a consistent level of electrical current which is not effected by fluctuations of the power source voltage. The choice of low levels of such current is dictated by the desire to increase the sensitivity of the device to the outside disturbances.

The biofeedback response signal is obtained from the sensing element 31 and taken through an amplifying phase consisting of a differential amplifier 34 and an amplifier 35. As a result, the signal is amplified with a total amplification factor of about 30 dB. The sensing element 31 is influenced by both the useful disturbances and random disturbances such as those from static electromagnetic fields. To eliminate such random disturbances, a precision differential amplifier 34 is used on a first phase of amplification. One possible type of such an amplifier may be INA 128UB by BUR BRAUN in which the signal voltage from the sensing element 31 is fed onto one input of the amplifier 34 while the other input is supplied with the same voltage after feeding it through the integrator 32. As a result, only the useful disturbance signal is allowed to go through to the next phase of amplification in the amplifier 35 while the noise signal is filtered out. Any appropriate commonly known amplifier can be used as an amplifier 35.

Comparator 36 can be of the type 521SA3 (made by NIIME company in Zelenograd, Russia) and is designed to transfer the analog signal from the amplifier 35 into a series of impulses such as for example in an A–D converter and then transmits it onto a galvanic decoupling unit 37 for further transformation.

The need for a galvanic decoupling unit 37 is dictated by the presence of random fluctuating electromagnetic noise fields from the power supply lines of the device itself as well as from other nearby located electrical devices. This device is designed to separate alternating component from direct current and contains an optical channel including a photodiode PhD265A and a emitter AL107B made for example by Diode company in Moscow, Russia.

The detector channel 38 is designed to increase the influence of the bio informational correlation between visual target outline and patient's image to the sensing element 31. Reception is conducted in the short wave range, preferably at a frequency of 1.45 GHz, which is known to be in the range of radiowave transmission by human organs and tissues. Reception element is made with the help of a logoperiodic antenna 38a which has a multi-turn spiral tapered design to ensure narrow direction of reception but in a wide range of transmission frequencies. The taper is oriented in such a way that its narrow portion is aimed directly at the operator 40.

The mixer 38b is mounted preferably directly onto the antenna 38a and comprises a series of diodes (such as the type AA123 made by NIIPP company in Omsk, Russia) onto which a voltage is fed from the heterodyne 38e. Such heterodyne is typically a sine voltage generator and is widely used in radio receivers. It is tunable simultaneously with the tuning of the oscillatory circuit of the receiver, to which the antenna is connected. This makes it possible to mark a stationary value of difference at a frequency between that of the received signal and the heterodyne signal in any position of the settings of a radio receiver. An example of an appropriate heterodyne is the one based on the diode of the type KA717B-4 produced by Nalchik's PP factory in Nalchik, Russia.

The rectifier 38c is designed to separate the low frequency phase from the useful signal, which is in turn fed into the discriminator 38d such as for example a differential amplifier INA128UB. Discriminator 38d subtracts the integrated signal from the raw signal and arrives at informational voltage bursts. Such voltage bursts are then fed back into the integrator 32 and further into the current source 33 which changes the value level of the current and shifts the power current of the sensing element 31. Such fluctuations of the current of the sensing element 31 ultimately effect the frequency spectrum of its operation and the frequency range of the useful signal produced thereby.

EXAMPLE OF OPERATION

For the induction of operator's consciousness, both the digital photograph of the patient and the realistic picture of human organ/tissue are required.

A digital photograph of a patient should be taken to include a patient's face and body. It is not absolutely required to use a new photograph every time when the diagnosis is performed, but the shorter the time gap between taking the photograph and performing the diagnosis, the more accurate the diagnosis result would be. The studies conducted by the inventor have shown that a recently taken picture (for example one month prior to evaluation) that represents specific features of the present status of the target can be used. The effective distance between the target and the image is not limited. And the response does not depend on the time when the picture was taken.

Pictures of human organ/tissue should look real and should be easy for the operator to recognize. According to the present invention, even the state of bio molecules or genetic materials of the patient can be evaluated using the picture of diagrammatic illustration of bio molecules or DNA.

In the operation of the remote diagnostic system of the present invention, the operator has a significant role and should actively participate in the diagnosis. It is important that the operator is aware of the presence of the sensor to detect his biofeedback signals in response to the display of the patient's image. Although there is a slight dependency on each operator's ability and knowledge, it is negligible if the operator understands the mechanism of operation and completes the brief session of appropriate training.

The remote diagnostic system of the present invention operates in the following way. Upon initiation of the diagnostic sequence, the CPU unit 10 provides graphic data of a photograph of the patient and a realistic picture of a target organ/tissue for which the diagnosis should be performed. The graphic data is transmitted to CIU unit 20 and displayed on the first and the second display device 21 and 22 of CIU unit 20. Operator 40 should concentrate on these images and by doing so, his consciousness and intuition is induced. As a result of this consciousness induction, certain biofeedback changes are formed around operator 40, which cause the changes in noise generating pattern in DEU unit 30. These changes are detected and transformed by DEU unit 30 to the CPU unit 10 as electrical signals, which are stored in a database system of CPU unit 10. According to the present invention, these signals reflect the functional state of the target organ/tissue of the patient. By comparing received signals with appropriate reference data, these signals can be used in diagnosis of functional state of a certain organ/tissue of a patient right at the time when the test is performed.

As a result of operation of the remote diagnostic system of the present invention, the states of various organs/tissues of the patient are stored in the CPU unit 10 as digital signals. By comparing them with the signals obtained from healthy organ/tissue, it is possible to evaluate the functional state of each organ/tissue of the patient. And also these signals can be used in differentiating the pathophysiologic state of the patient's organs by comparing them with standard signals obtained from volunteers who have been diagnosed as having certain diseases in organ/tissue. Such comparison also allows determining the degree of pathology and state of disease development of the organ/tissue.

Although the invention herein has been described with respect to particular embodiments, it is understood that these embodiments are merely illustrative of the principles and applications of the present invention. For example, a different type of detection/evaluation unit or a triggering sensor can be used to detect the biofeedback response of the operator. Other types of biofeedback response signals may also be considered for the purposes of the invention such as brainwaves and alike. Also, it is believed that depending upon the design of stimuli, a variety of systems such as showing the pathological status of organs of a patient on the image or indicating the location of human or lost articles on the maps can be developed. It is therefore to be understood that numerous modifications may be made to the illustrative embodiments and that other arrangements may be devised without departing from the spirit and scope of the present invention as defined by the appended claims.

What is claimed is:

1. A medical diagnosis biofeedback system based on a patient image comprising:

a central processing unit including a situation-generating sub-system in a computer readable memory for producing a series of predetermined patient-specific visual images including at least an outline of a target area of diagnostic interest, said central processing unit also including means for receiving a biofeedback signal from a user exposed to said images;

a consciousness induction unit including a first means for visually displaying the patient image and a second means for visually displaying the outline of a target area of diagnostic interest to the user to cause a heightened state of consciousness and intuition of the user, and a detection/evaluation unit equipped with noise generator that remotely senses the noise changes constituting the biofeedback response of the user, wherein a biofeedback loop is formed between said central processing unit sending said predetermined patient-specific visual images to said consciousness induction unit to be displayed to the user, said detection/evaluation unit sensing the response of biofeedback of the user representing the user's response to said images, said detection/evaluation unit further generating an electrical signal reflecting said biofeedback response and sending said electrical signal back to said central processing unit.

2. The medical diagnosis biofeedback system based on a patient image as in claim 1, wherein said patient-specific visual images include the patient image in addition to the outline of a target area of diagnostic interest.

3. The medical diagnosis biofeedback system based on a patient image as in claim 2, wherein said patient's image is a digital photograph of the patient.

4. The medical diagnosis biofeedback system based on a patient image as in claim 2, wherein said outline of a target area is a picture of a human organ or tissue.

5. The medical diagnosis biofeedback system based on a patient image as in claim 3, wherein said digital photograph of the patient is being displayed by said first means and said outline of a target area is being respectively displayed by said second means.

6. The medical diagnosis biofeedback system based on a patient image as in claim 1, wherein said first means is adapted to display continuously the image of the patient while said second means is adapted to display a succession of outlines of various target areas.

7. The medical diagnosis biofeedback system based on a patient image as in claim 1, wherein said first and said second means are computer monitors.

8. The medical diagnosis biofeedback system based on a patient image as in claim 1, wherein said first and said second means are slide projectors.

9. The medical diagnosis biofeedback system based on a patient image as in claim 1, wherein said electrical signal generated by said detection/evaluation unit is used in diagnosis of a functional state of a target area of said patient.

10. The medical diagnosis biofeedback system based on a patient image as in claim 1, wherein said central processing unit is adapted to record said electric signals from said detection/evaluation unit into a database and for comparison of said electric signals against previously known electrical signals.

11. The medical diagnosis biofeedback system based on a patient image as in claim 1, wherein said detection/evaluation unit includes a triggering sensor with a noise generator, said biofeedback response of the user including a noise change in said triggering sensor.

12. The medical diagnosis biofeedback system based on a patient image as in claim 1, wherein said consciousness induction unit further comprising a third means for enhancing the biofeedback response from the user by transmitting to the user of a series of predetermined stimuli to induce consciousness thereof.

* * * * *